United States Patent
Mouton

(10) Patent No.: US 7,828,813 B2
(45) Date of Patent: Nov. 9, 2010

(54) GASTRIC BAND

(75) Inventor: Didier Mouton, Saint Priest en Jarez (FR)

(73) Assignee: Surgical-IOC, Saint-Etienne (FR)

(*) Notice: Subject to any disclaimer, the term of this patent is extended or adjusted under 35 U.S.C. 154(b) by 1325 days.

(21) Appl. No.: 10/478,989

(22) PCT Filed: May 31, 2002

(86) PCT No.: PCT/FR02/01848

§ 371 (c)(1),
(2), (4) Date: Nov. 26, 2003

(87) PCT Pub. No.: WO02/096326

PCT Pub. Date: Dec. 5, 2002

(65) Prior Publication Data

US 2004/0230137 A1   Nov. 18, 2004

(30) Foreign Application Priority Data

Jun. 1, 2001 (FR) ................................ 01 07416

(51) Int. Cl.
*A61B 17/08* (2006.01)
(52) U.S. Cl. .................... 606/151; 606/157; 600/37
(58) Field of Classification Search .......... 606/151, 606/153, 157, 158, 201, 202.203; 600/37; 24/16 PB; 2/311, 321
See application file for complete search history.

(56) References Cited

U.S. PATENT DOCUMENTS

| | | | | |
|---|---|---|---|---|
| 4,263,697 A | * | 4/1981 | Speedie ................... | 24/30.5 P |
| 4,592,339 A | | 6/1986 | Kuzmak et al. | |
| 4,676,535 A | * | 6/1987 | Mautner ................... | 292/320 |
| 4,696,288 A | | 9/1987 | Kuzmak et al. | |
| 4,817,901 A | * | 4/1989 | Kuo ........................ | 248/230.8 |
| 5,074,868 A | * | 12/1991 | Kuzmak ................... | 606/157 |
| 5,160,338 A | * | 11/1992 | Vincent .................... | 606/157 |
| 5,449,368 A | * | 9/1995 | Kuzmak ................... | 606/157 |
| 5,517,727 A | * | 5/1996 | Bernard et al. ........... | 24/16 PB |
| 5,524,463 A | * | 6/1996 | Schenkel et al. .......... | 70/57.1 |
| 5,601,604 A | * | 2/1997 | Vincent .................... | 606/216 |
| 5,658,298 A | * | 8/1997 | Vincent et al. ............ | 606/139 |
| 5,819,375 A | * | 10/1998 | Kastner ................... | 24/16 PB |
| 5,881,435 A | * | 3/1999 | Jermyn, Jr. ............... | 24/16 PB |
| 6,102,922 A | | 8/2000 | Jakobsson et al. | |

(Continued)

FOREIGN PATENT DOCUMENTS

DE       90 14 048 U      12/1990

(Continued)

*Primary Examiner*—Darwin P Erezo
(74) *Attorney, Agent, or Firm*—Dowell & Dowell, P.C.

(57) ABSTRACT

The invention concerns a band not provided with a dilatable portion, characterized in that it comprises different successive separate zones (A, B, C) formed on its entire developed length, while forming a single-piece and single-unit assembly, and its two ends (1a), (1b) are specifically configured to form flexible nesting and position-locking male-female parts by defining a first head zone (A) and a second rear and anchoring zone (B) forming a main tip and integrated into each other, and between said two zones, the ring comprises a third intermediate connecting zone (C) with solid cross-section over the main part of its length, designed to be more specifically pressed on the part of the stomach to be enclosed.

14 Claims, 8 Drawing Sheets

U.S. PATENT DOCUMENTS

| | | | | |
|---|---|---|---|---|
| 6,226,839 B1 * | 5/2001 | Sayegh | | 24/16 PB |
| 6,484,367 B1 * | 11/2002 | Caveney et al. | | 24/16 PB |
| 6,676,674 B1 * | 1/2004 | Dudai | | 606/151 |
| 6,966,875 B1 * | 11/2005 | Longobardi | | 600/31 |

FOREIGN PATENT DOCUMENTS

| | | | |
|---|---|---|---|
| DE | 197 51 733 A | | 12/1998 |
| EP | 1 036 545 A | | 9/2000 |
| FR | 2 798 280 | | 9/1999 |
| FR | 2 799 118 | | 4/2001 |
| WO | WO 94 27504 A | | 12/1994 |
| WO | WO 01/24742 | * | 4/2001 |

* cited by examiner

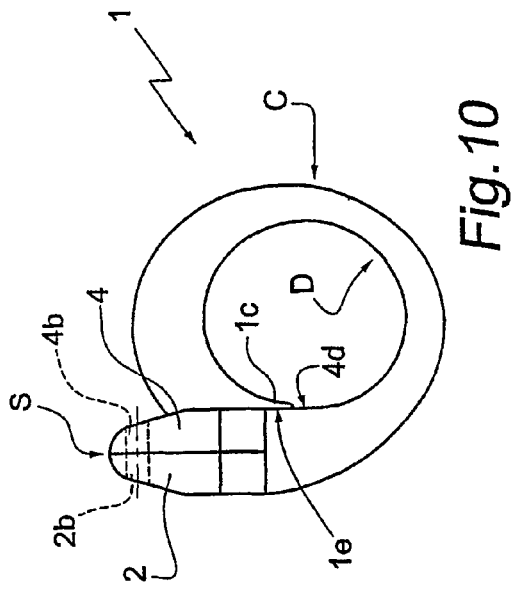
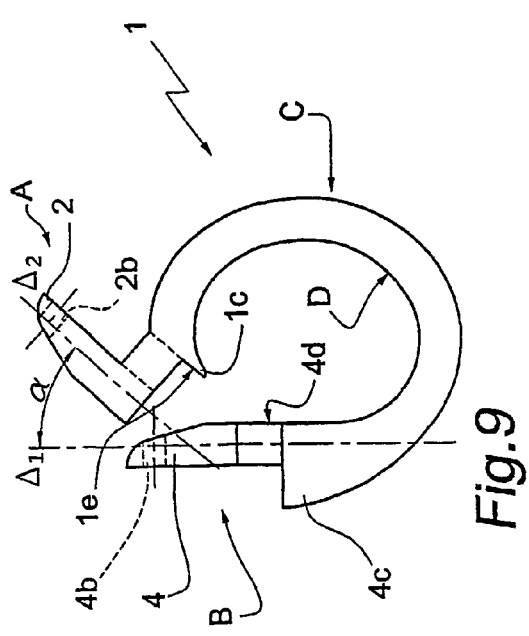
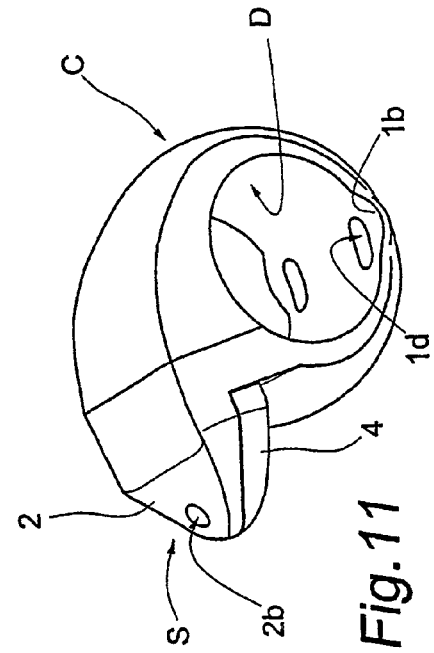

GASTRIC BAND

BACKGROUND OF THE INVENTION

1. Field of the Invention

The invention relates to the technical sector of gastric bands and similar means capable of encircling a stomach part in order to ensure an effect of shrinkage of the stomach at a given place, within the framework of the treatment of obesity, and this after failure of medical therapeutics such as diets, followed by nutritionists, programmes of physical exercises, slimming cures, and criteria of the ANAES (BMI and Comorbidity).

2. Description of the Related Art

According to the prior art, different types of gastric bands are known, which are, furthermore, associated with other means such as fluid-dilatable balloons, as described in DE-U-9724127 or WO-A-9427504, or in association with a tube with light flux, as described in U.S. Pat. No. 4,696,288. These technologies are expensive to carry out. The fitting of these bands remains random by the effect of the slide of the band on the stomach, and especially when associated hiatal hernias exist.

One of the problems raised at the origin of the invention resides in the operation of closure of the band which is not always easy to carry out and with security of the connection.

Another problem is the necessity of a monitoring of the inflation of the balloon of the known bands by a vulnerable outside system which causes discomfort for the majority of patients operated on. This system includes the use and holding of a sub-cutaneous box, with risk of contamination by the needle. This involves specific precautions. In addition, these bands are particularly uncomfortable for the patient, being a source of pain, of leakage, as there are risks of breaking of the flow, the inflation of the balloon involving a pressure. Moreover, the inner surface of the bands with dilatable balloon is sometimes irregular when the balloon is not dilated, hence a risk of lesion or irritation of the gastric wall. FIG. 1 shows such a gastric band. The fitting of these gastric bands as described hereinbefore is effected within the framework of a vertical gastroplasty.

The use of strips, disposed in a substantially horizontal plane, is also known. However, this technique also presents drawbacks, namely: these strips, made for example of polypropylene netting, cause incrustations of matter in the wall of the stomach, with a detrimental effect preventing the ablation of the bandage thus made in the event of a decision of reversibility (creation of a fibrous tunnel facilitating the ablation of the material and protecting the gastric muscle).

Furthermore, the positioning of the gastric band thus described creates a horizontal partition creating a configuration of the stomach in two parts, or sacs, with slide of the band due to the risks of dilatation of the lower sac.

FR-A-2 798 280 also discloses a gastric band not provided with a dilatable balloon and made in the form of a tube provided with a flat portion for abutment against the gastric wall. This band must be maintained in closed configuration by means of a suture strand. Its diameter in closed configuration depends on the tension given to the suture by the surgeon, with a non-guaranteed reproducibility.

Finally, EP-A-1 036 545 discloses a non-dilatable gastric band provided with an opening for passage of one of its ends in closed configuration. The locking obtained is not optimum.

SUMMARY OF THE INVENTION

The solution employed according to the Application is such as to respond to the problems raised, from an original concept of production and a method of fitting which guarantees the position of the band in place.

The solution aimed at carried out a method of fitting, specific of the product and which has the result of obtaining rapid effects on the patient's obesity.

According to the invention, a gastric band not provided with a dilatable part is made of an elastomeric, particularly siliconed material, presents a flexibility of deformability and comprises different successive separate zones formed on its entire developed length, while forming a single-piece and single-unit assembly, these zones including two end zones shaped specifically to constitute flexible nesting and position-locking male-female parts and, between these two zones, an intermediate connecting zone of solid cross-section over the main part of its length, designed to be more specifically in simple abutment on the part of the stomach to be encircled. This band is noteworthy in that the end zones define, on the one hand, a first head zone provided with a curved profiled tab and, on the other hand, a second rear end anchoring zone forming main tip, these zones being adapted to integrate into each other, by introduction of the tip of the anchoring zone in an opening defined between two lateral walls connecting the tab to the intermediate zone.

BRIEF DESCRIPTION OF THE DRAWINGS

In order to render its object more concrete, the invention is illustrated in non-limiting manner in the Figures of the drawings, where:

FIG. 4A is a section along line IV-IV in FIG. 4.

FIG. 9 is a side view, before use, of a band according to a second form of embodiment of the invention.

FIG. 10 is a side view of the band of FIG. 9 in closed configuration, and

FIG. 11 is a view in perspective of the band of FIGS. 9 and 10 in closed configuration.

DETAILED DESCRIPTION OF THE PREFERRED EMBODIMENTS

Figure 1:
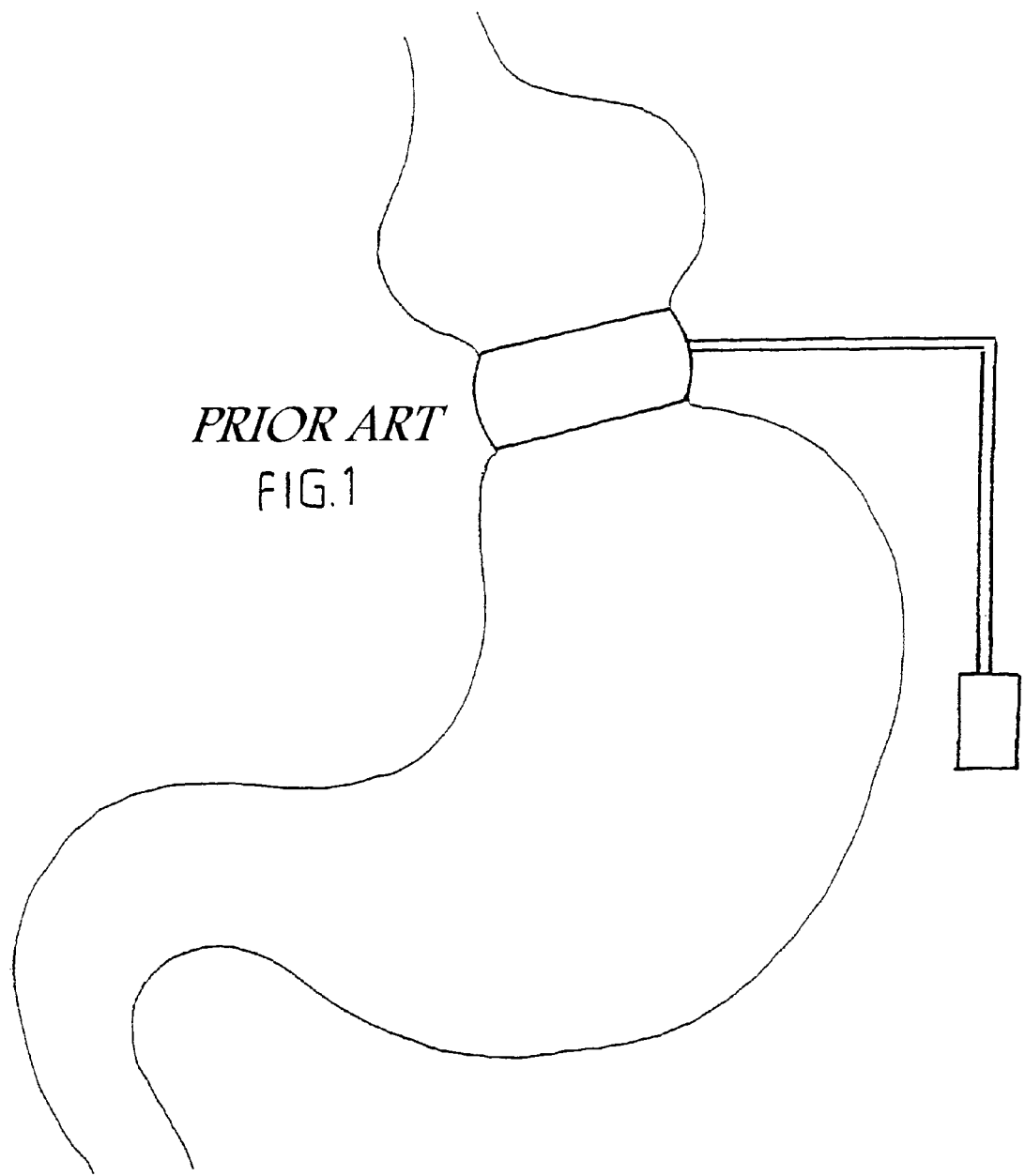
FIG. 1 is a view of schematic nature illustrating the fitting of a gastric band, in accordance with the prior art.
Figure 2:
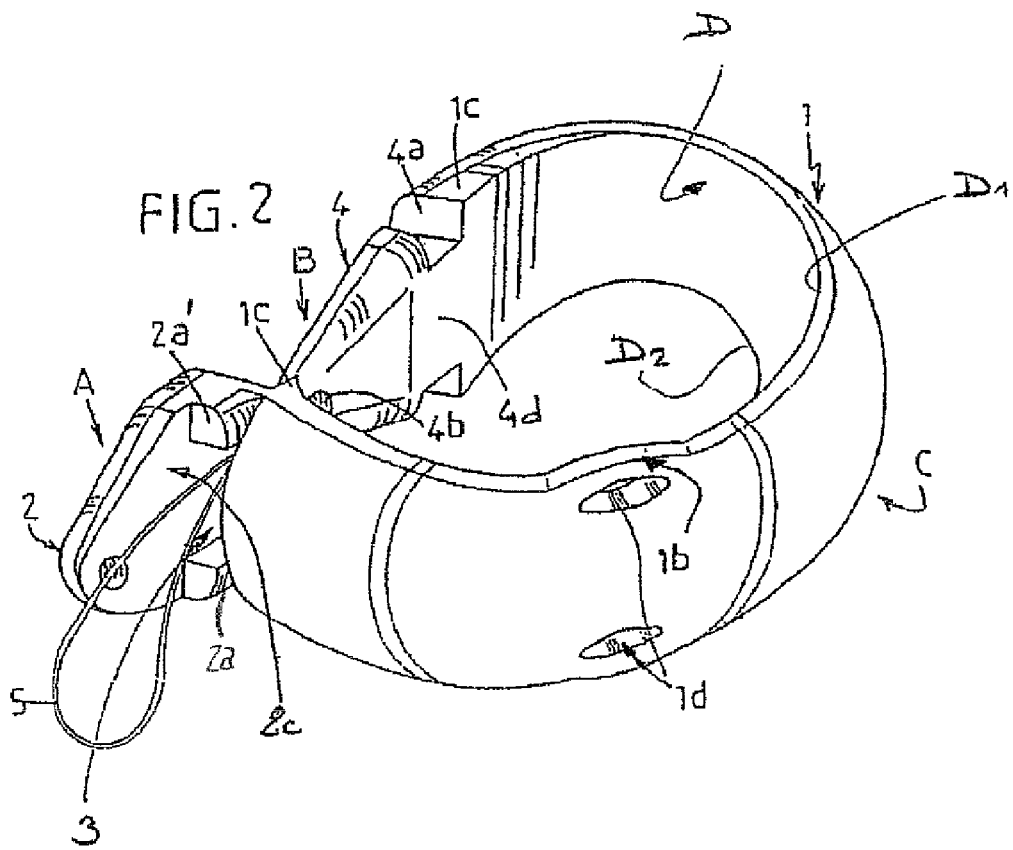
FIG. 2 is a view in perspective before tightening and closure of the band, according to the invention, the band being shown as such and not positioned.
Figure 3:
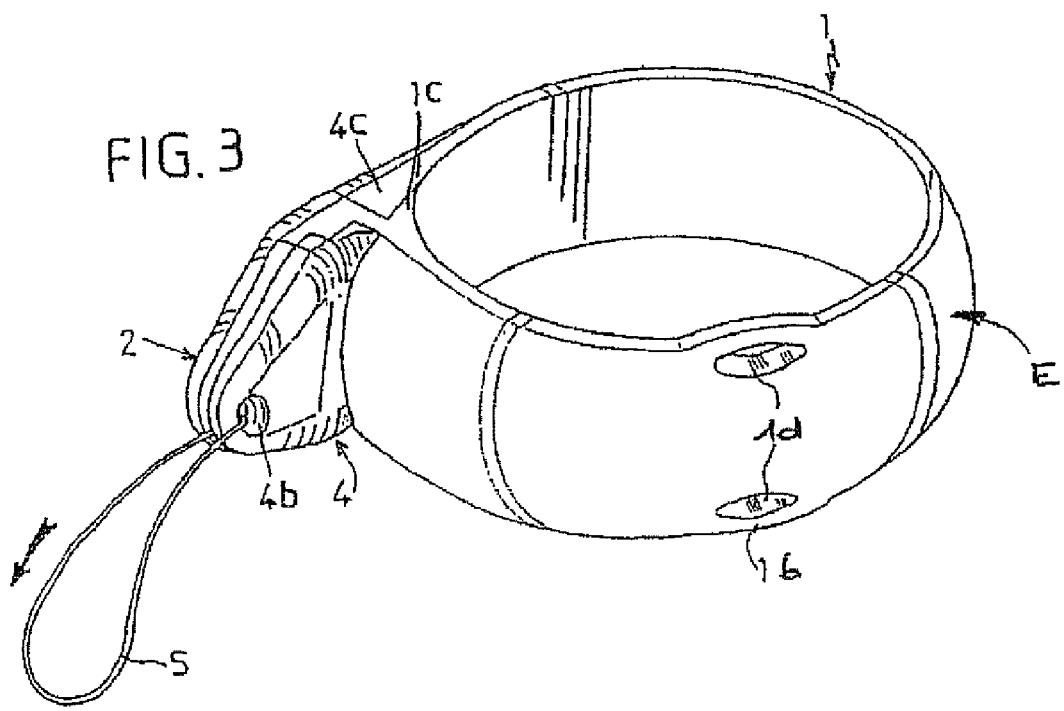
FIG. 3 is a view in perspective of the gastric band defined in accordance with FIG. 2, after closure.

In order to render the object of the invention more concrete, it is now described in non-limiting manner, illustrated in the Figures of the drawings.

The gastric band according to the invention is generally referenced 1 and is made of a moulded, elastomeric material in one piece. It presents a certain elasticity with capacity of deformation. In closed position, it presents the configuration of a collar, surrounding the desired part of the stomach. This band is preferably made of medically implantable siliconed material, such as that known on the market under the Trademark "NUSIL". This material is radio-opaque and biocompatible in order to be implantable in the human body, thus responding to the requirements of compatibility and without being destructible. This band presents a memory of shape in order to return it naturally into position of collar before closure, as represented in FIG. 9 of the drawings, or substantially.

By its constituent material, elastomer and preferably siliconed, it offers a certain flexibility of deformability, so as to allow introduction thereof in the desired place and to be deformed in order to constitute a configuration of collar and follow the encircled shapes as well as possible, allowing a mode of anchoring which is characteristic of the invention.

In the state of implementation, the band is unfolded over the whole of its length. In the state of closure, it is folded in the manner of a collar and, according to the invention, in an assembly and fixation which is reversible but secure.

The band 1 is not provided with a dilatable balloon, which gives it an increased reliability with respect to the known devices, particularly disclosed by WO-A-94/27504. It is therefore not adjustable in diameter.

It is noteworthy in that it comprises different, successive, separate zones formed over the whole of its developed length, while forming a one-piece and unitary assembly, avoiding zones of weakness, such as can exist in devices with dilatable balloon. The two ends of the band 1 are formed specifically in order to constitute flexible-nesting and position-locking male-female parts, by defining a first head zone A and a second rear end anchoring zone B, forming main tip, these zones integrating in each other, as will be specified hereinafter.

Between the two afore-mentioned zones, the band comprises a third intermediary zone C of length (sic) and for connection. This zone is intended to be more specifically in abutment on the part of the stomach to be encircled. The internal face D of the band and the non-traumatic edges $D_1$ and $D_2$ are smooth, which is to be compared with the fact that no dilatable balloon is provided on this face.

On a part of the intermediary connection zone C, the band internally presents projecting shapes 2b allowing the contact in punctual pressure on the stomach part opposite, with an anti-slide effect. There is then provided in this part the formation of two cavities 1d in the thickness of the band allowing threading of complementary ligaturing strands L intended for the complementary fixation of the band with respect to its environment (gastric wall or grainy felting) avoiding its slide and possible tipping. The part 1b is swollen with respect to the rest of the wall C and constitutes projecting shapes for complementary punctual abutment on the stomach, without there being any adhesion to the wall of the stomach opposite.

The visible outer part E of the band is substantially convex over the whole of its length and in a transverse plane.

As is visible in FIG. 4A, part C is of solid cross-section, except at the level of the cavities 1d. This solid, i.e. one-piece, unitary and massive, nature gives it an increased mechanical resistance and a good elasticity. In effect, the solid nature of this cross-section guarantees the stability in time of the calibration obtained with the band 1 which, due to the elasticity and the memory of its constituent material, resumes its nominal geometry after possibly having been deformed upon passage of food. This solid nature also induces a homogeneity during deformation of the band, in the course of positioning or once fitted.

The head zone A is established with a profiled tab 2 which is curved and disposed at the front end of the body of the band, being connected to the part C by the join of two lateral walls 2a, leaving therebetween an opening allowing the passage and the introduction and positioning of the other end in the form of a tip 4.

Figure 4:
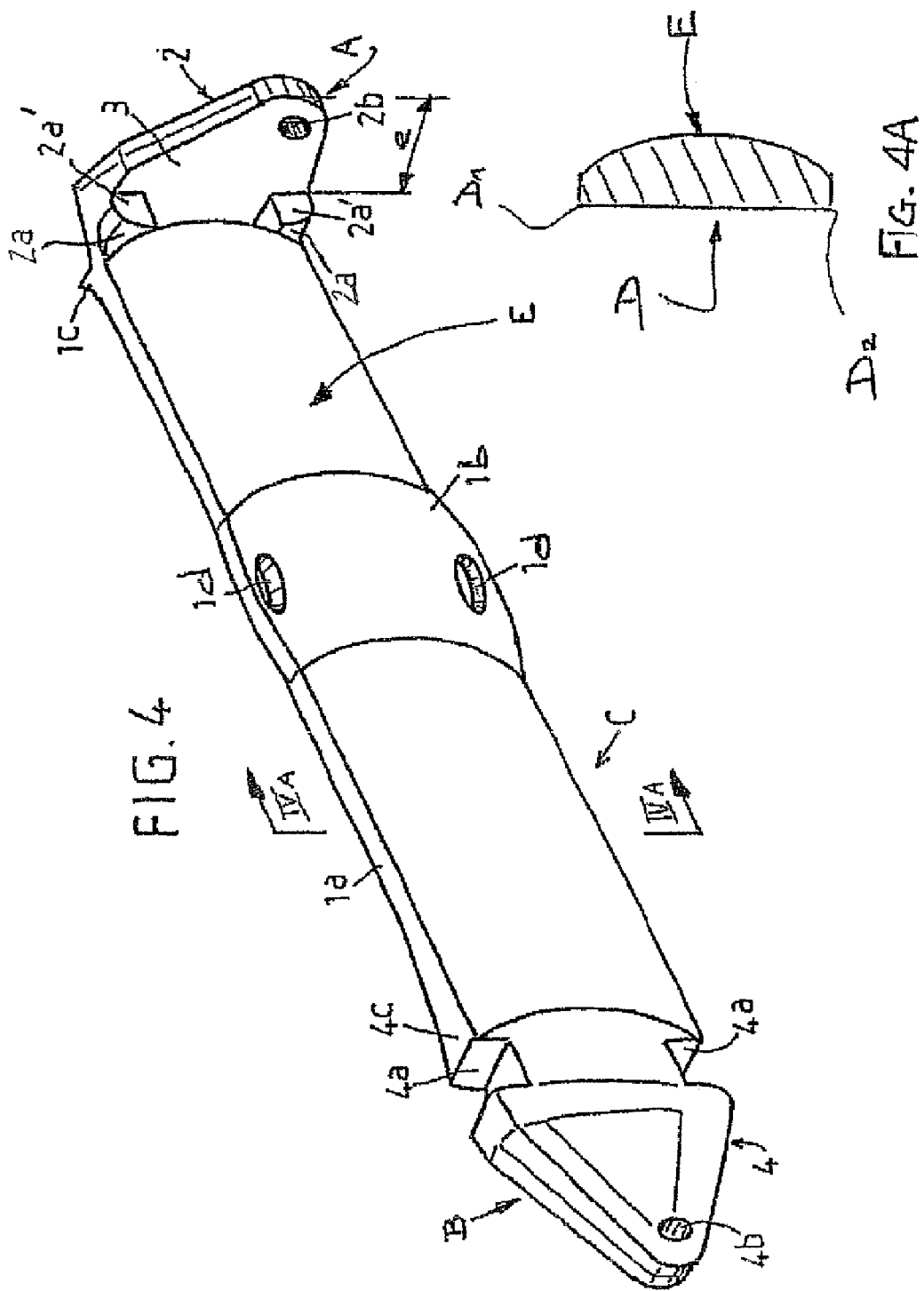
FIG. 4 is a view in perspective of the band shown flat and unfolded, in order to illustrate all of its characteristics.

The tab 2 is substantially planar and extends in a plane substantially perpendicular to the principal direction of the part C in the configuration of FIG. 4.

More specifically, the main tab 2 presents, in extension, walls for connection with two parallel projections 2a defining a channel 3 for passage of the second end, in the form of a tip 4. Furthermore, the main tab presents stop faces 2a' on the parallel projections 2a, as will be specified hereinbelow. This end or tab 2 of the band 1 presents a secondary tip shape, of triangular aspect with a visible flat face of length e equal to the length of the zone from the stop faces 2a' of the parallel projections 2a to the end of the tab 2 furthest from the connecting part C, as shown in FIG. 4. At the end, the perforated tab presents a transverse opening 2b for the passage of a draw loop 5.

In parallel, the rear end 4 of the band presents a main tip shape having a profile of dimensions corresponding to those of the tip shape established on the front tab. Between the tip shape 4 of the anchoring part and the zone C are formed two grooves 4a, profiled and opposite, of which the depth corresponds in fact to the thickness of the projections 2a established on the main tab.

The end of the main tip shape 4 also presents an opening 4b for the passage of a ligature or draw loop.

It will thus be understood, with reference to FIGS. 2, 3, 7 and 8, that the closure of the gastric band is effected by introduction of the main tip shape of the rear end 4 of the band in the opening or channel 3 for passage located in the zone of connection of the front tab and of the front end of the band.

The main rear tip shape 4 is pulled by a draw loop 5 by means of an instrument for passage which causes it to be elastically deformed in order to traverse the opening passage 3 and to anchor on the front tab 2 after juxtaposition.

The afore-mentioned grooves 4a then surround the projecting parts 2a of the front tab 2, while the main and secondary shapes in tip form are juxtaposed against each other.

The openings 2b and 4b then lie opposite each other, with the result that the draw loop 5 may also serve as means for ligaturing and for fixation.

In the second form of embodiment of the invention shown in FIGS. 9 to 11, elements similar to those of the first embodiment bear identical references.

As is more particularly visible in FIG. 9, the band 1 presents, before use and as a result of its process of manufacture by moulding, an open shape in which the tip 4 substantially extends the intermediate zone C, in a direction $A_1$, while the tab 2 extends substantially in a direction $A_2$ making an angle α of the order of 45° with the direction $A_1$.

As previously, the inner surface D of the part C is smooth, which is to be compared with the fact that the band 1 is not provided with a dilatable balloon and has a solid section over the main part of the length of the part C, except for the zones 1b where the cavities 1d are formed.

When the band is closed, as shown in FIGS. 10 and 11, the tab 2 and the tip 4 together form a projecting part S of which the outer edges are rounded and which is non-traumatic. In addition, in this configuration, the inner face D of the zone C is substantially circular, this allowing a precise calibration of a patient's stomach.

In addition and in accordance with an advantageous complementary arrangement, the inner face D of the band presents on the head A side a profile 1c in line with the head, oriented thereopposite and in a subjacent plane, so as to constitute a plane of abutment 1e and of reliability of the part 4d of the band adjacent the grooves 4a. In this way an effect of increased stability is obtained, and an overlapping, by the profile 1c, of the zone of join between the zones A and B, seen from inside the band. The risks of injury or of irritation of the gastric wall are thus limited.

Furthermore, the section 4c of the part of the formed band in the vicinity of the tip 4 may be thicker in order to ensure a better holding.

The gastric band thus produced is therefore easy to place in position. It is non-dismountable per se, unless the operator deforms the part of the tip 4 of the rear end B of the band in order to withdraw it and direct it towards the opening 3 for introduction formed on the front part A thereof. The draw loop may serve a complementary function of fixation by ligature if necessary after introduction in the openings 2b and 4b formed on the tip parts of the band. The band offers double security by the specific locking of the tip parts together, of the tab and the rear end of the band, on the one hand, and, on the other hand, of the groove-projection 4a-2a connection.

The band thus having been defined in its structural characteristics, the method of fit and the place of positioning of the band on the stomach will now be set forth with reference to FIGS. 5 to 8 of the drawings, and this in order to respond to the desired effects of gastric reduction for the treatment of obesity.

Figure 5:
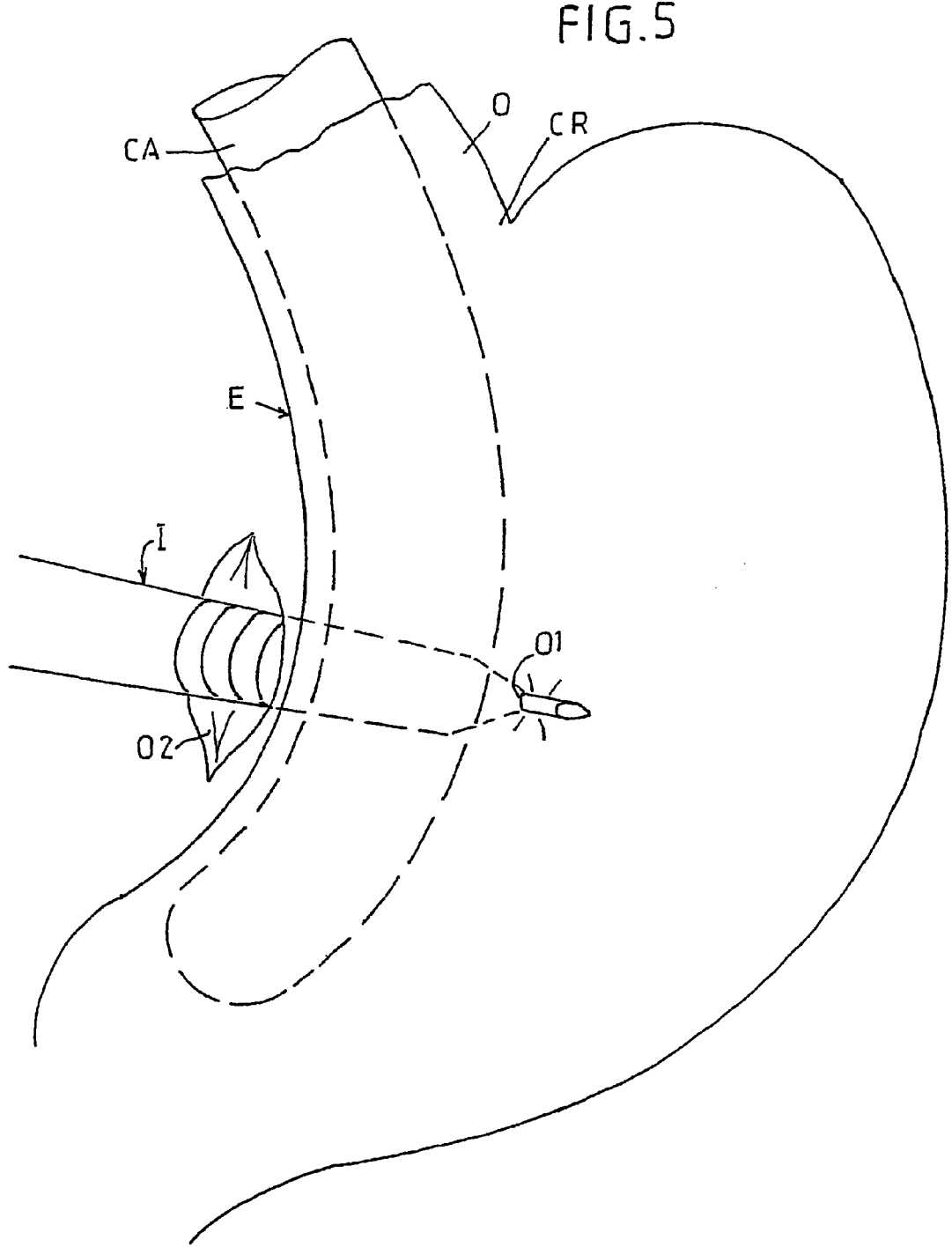
FIGS. 5, 6, 7 and 8 illustrate the different phases of the method of positioning the band around the specific place of the stomach.
Figure 6:
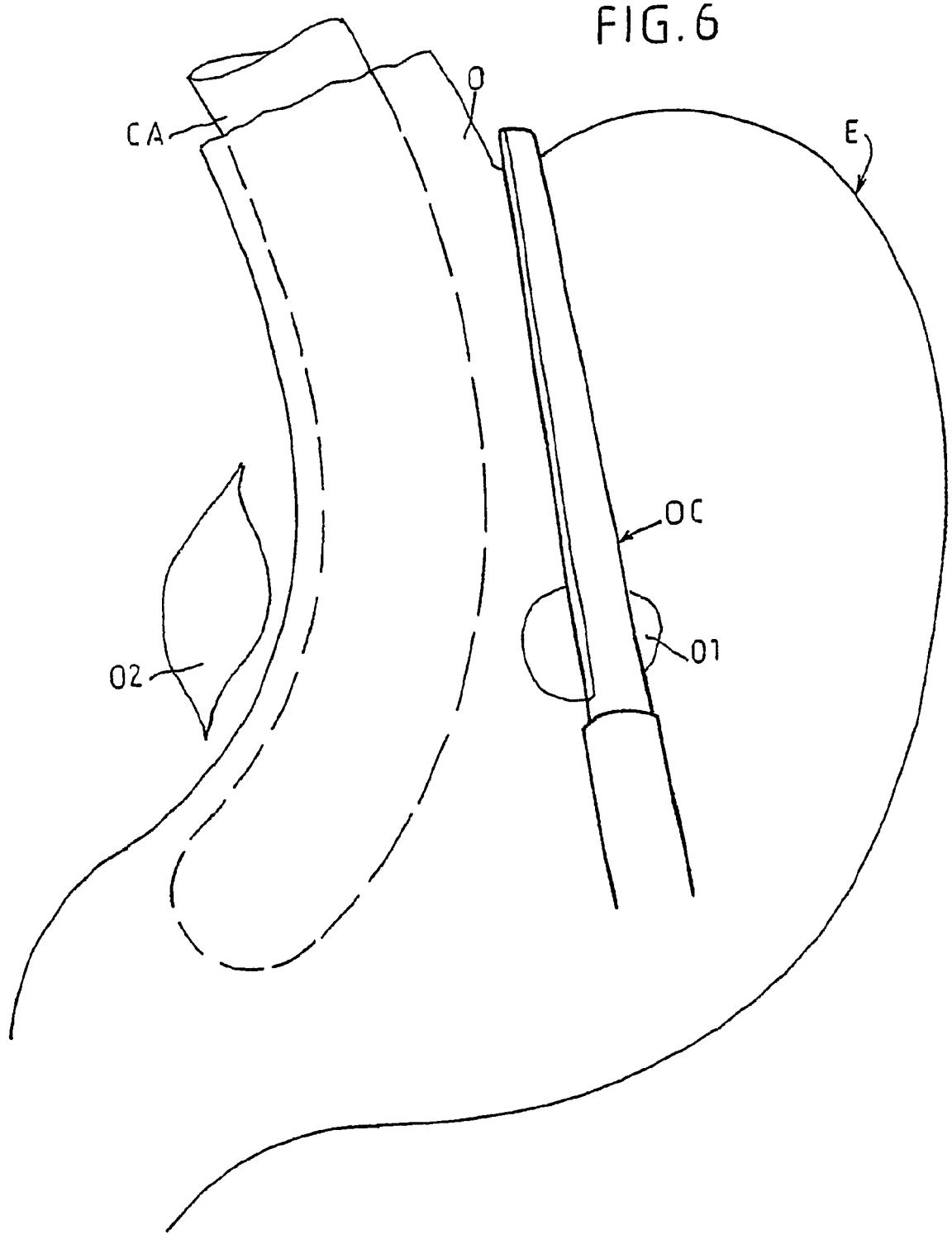

According to the invention, a gastric tube called 33 French Faucher tube (CA) must firstly be introduced through the patient's mouth, to arrive in the stomach (E). In order to reduce the useful volume of the stomach, the intervention should take place on the upper stomach part which presents an orifice called cardia (CR) where the oesophagus (O) opens out. This orifice defines with the upper part of the stomach a cavity of more or less great capacity in individuals (FIG. 5). The operator, with the aid of an instrument (I), will perforate the stomach wall at a first site (O1), between 6 and 8 cm beneath the cardia. A second cut out separates the two gastric parts in a plane which is vertical, and this with the aid of an instrument known to the person skilled in the art.

This second cut out (O2) is effected near the positioning of the gastric tube in the stomach (FIG. 5). The operator then proceeds, with the aid of a cutting tool (OC), with the vertical partition of the stomach so as to create a new gastric sac near the lesser gastric curvature and will be of small volume 50 to 70 ml.

Figure 7:
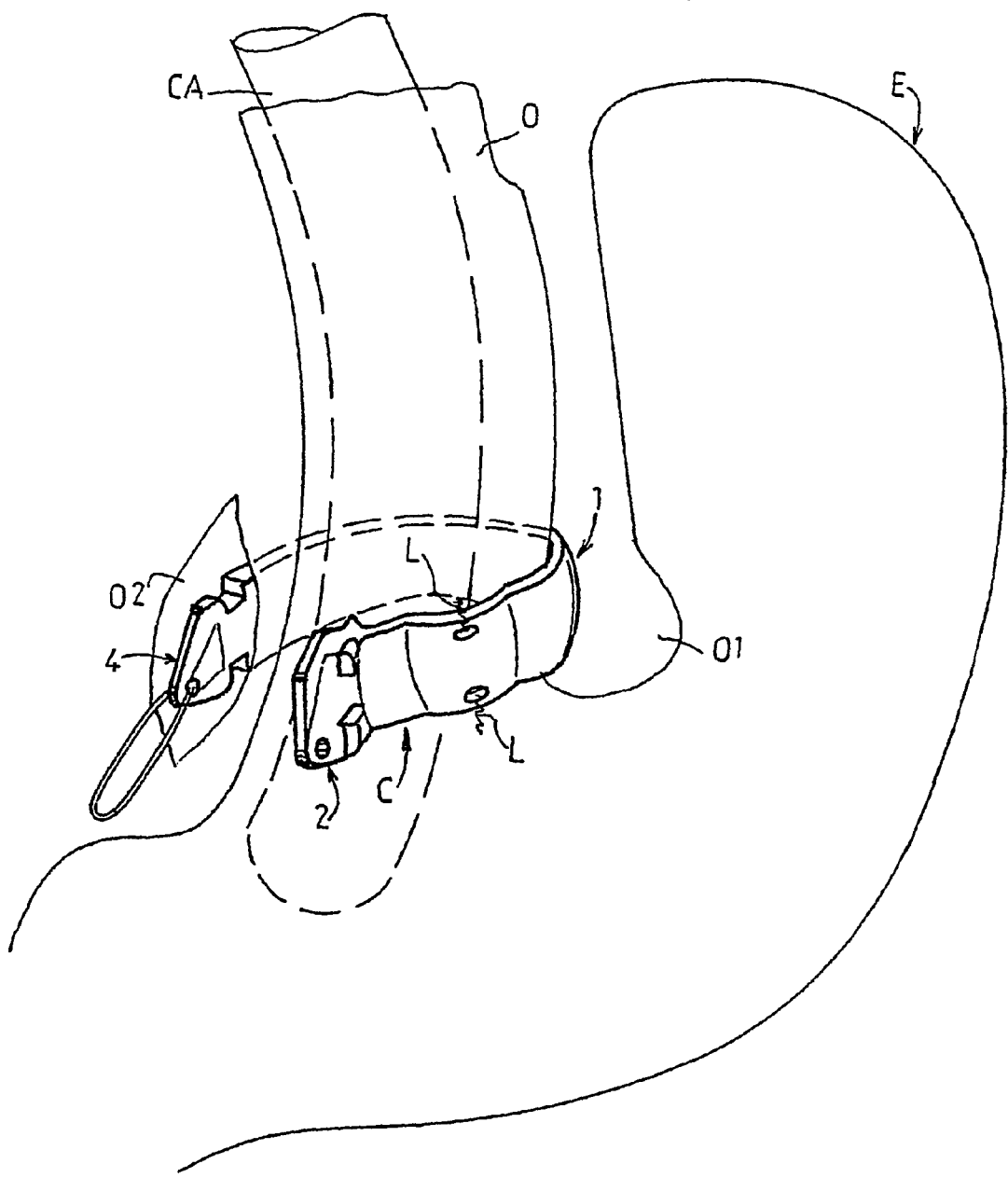
Figure 8:
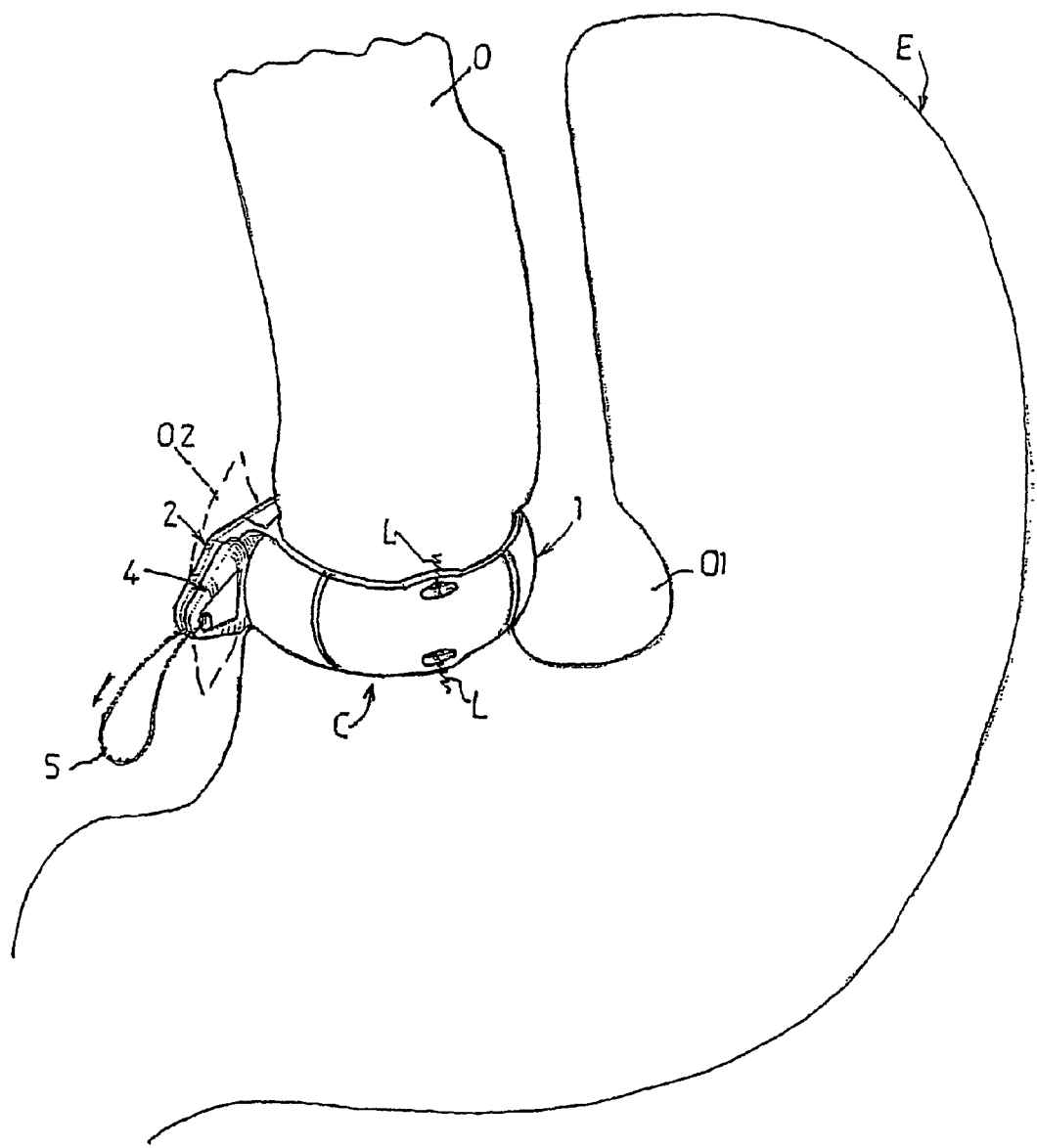

Its emptying will be effected through an orifice which will have to be calibrated. The operator introduces the band (1) which is in developed position with the aid of a complementary gripping instrument (FIG. 7). With the aid of a gripping element, the operator will grip the draw loop (5) and introduce the rear end of the band in the anchoring front tab part, and then ensure closure thereof, as shown in FIG. 8 of the drawings. It then suffices to add one or two complementary ligaturings (L) established from the cut outs formed in the intermediate zone of the band, these stitches being fixed on the environment of the stomach, the Faucher calibration tube is then withdrawn.

The advantages of the invention are numerous and the following are emphasized in particular:
  the quality of the band and of its secured position on the stomach,
  its reliability of fit, its easy accessibility, and its rapid dismantling.

Its characteristics correspond to the necessity of an invulnerable calibration, non-aggressive for the gastric wall avoiding any slide and erosion. This intervention may be carried out in the event of hiatal hernia, a pathology which is a pitfall for the use of a gastric band for horizontal partition.

This intervention is reversible and the band may be recovered for a fresh use.

The band is well tolerated due to its constitution and does not risk causing undesirable local inflammations. Furthermore, there is no risk of traumatism, as the band is used alone without other accessories, as is often the case according to the prior art.

The invention claimed is:

1. A gastric band not provided with a dilatable part and made of an elastomeric material presenting a flexibility of deformability, comprising: a single-piece assembly made from said elastomeric material such that the gastric band resumes an original geometry after being deformed upon passage of food and including different successive separate zones formed on an entire length of the gastric band, said zones having two end zones shaped specifically to constitute flexible nesting and position-locking male-female parts and, between said end zones, an intermediate connecting zone of solid cross-section over a main part of a length of said intermediate connecting zone and designed to be in simple abutment on a part of a stomach to be encircled, wherein said end zones define, on a first end, a head zone provided with a curved profiled tab extending substantially perpendicularly from the length of said intermediate connecting zone and having lateral walls each with a stop face thereon, a secondary tip with a triangular flat face, and a transverse opening for passage of a draw loop and, on a second end, a rear end anchoring zone forming a main tip having a transverse opening corresponding to said transverse opening of said tab for passage of a draw loop between said openings of said main tip and said tab, said zones being adapted to integrate into each other by introduction of said main tip of said rear end anchoring zone in an opening defined between said lateral walls connecting said tab to said intermediate connecting zone.

2. The gastric band according to claim 1, wherein said intermediate connecting zone has, over a part of the length of said intermediate connecting zone, projecting shapes for contacting a part of the stomach to provide an anti-slide effect, said projecting shapes being provided with two cavities in a thickness of the gastric band, said cavities allowing a threading of complementary fixation strands for positioning the gastric band with respect to the stomach and for avoiding tipping of the gastric band.

3. The gastric band according to claim 1, wherein an outer part of said intermediate connecting zone of the gastric band is substantially convex over the length of the length of said intermediate connecting zone and in a transverse plane.

4. The gastric band according to claim 1, wherein the elastomeric material is a shape-memory material so that the gastric band returns substantially to a position of a collar before closure.

5. The gastric band according to claim 1, wherein said main tip has a shape with a profile of dimensions corresponding to said tab, and wherein said main tip includes, at a rear of said main tip of said rear end anchoring zone, two opposite profiled grooves, said profiled grooves each having a depth which corresponds to a thickness of two projections formed on said tab.

6. The gastric band according to claim 1, wherein an inner face of the gastric band has, at said head zone, a profile that provides a plane for abutment adjacent grooves formed on said main tip.

7. The gastric band according claim 1, wherein, before closure and when no outside effort is exerted on the gastric band, said head zone and said rear end anchoring zone extend in two directions ($D_1$, $D_2$), which are not parallel.

8. The gastric band according to claim 7, wherein, in a closed configuration of the gastric band, an inner face is substantially circular.

9. The gastric band according to claim 1, wherein said openings in said head zone and in said main tip are opposite each other in a closed configuration of the gastric band.

10. The gastric band according to claim 1, wherein, when the gastric band is closed, said tab and said main tip together form a part projecting with respect to said intermediate connecting zone.

11. The gastric band according to claim 10, wherein, when the gastric band is closed, said tab and said main tip are substantially parallel and in abutment against each other.

12. The gastric band according to claim 10, wherein said tab extends in a plane substantially perpendicular to a principal direction of said connecting intermediate zone when the gastric band is open.

13. The gastric band according to claim 1, wherein the elastomeric material is a silicon material.

14. The gastric band according to claim 1, wherein said tab has a generally triangular shape, and said main tip has a corresponding generally triangular shape.

* * * * *